United States Patent [19]

Weidemann

[11] Patent Number: 5,267,087
[45] Date of Patent: Nov. 30, 1993

[54] DIAGNOSTIC DEVICE FOR THE EXAMINATION OF BIOLOGICAL MATERIAL

[76] Inventor: Peter Weidemann, Dingstätte 34, 2080 Pinneberg, Fed. Rep. of Germany

[21] Appl. No.: 830,198

[22] Filed: Jan. 31, 1992

[30] Foreign Application Priority Data

Apr. 4, 1991 [DE] Fed. Rep. of Germany ....... 9104079

[51] Int. Cl.⁵ ............................................. G02B 21/00
[52] U.S. Cl. .................................... 359/801; 359/385; 359/800; 359/804; 359/390; 422/82.05
[58] Field of Search ............... 359/798, 799, 800, 801, 359/802, 804, 805, 809, 810, 385, 389, 390; 422/82.05

[56] References Cited

U.S. PATENT DOCUMENTS

| 2,892,274 | 6/1959 | Afton | 359/801 |
| 3,582,181 | 6/1969 | Dolores | 359/799 |
| 4,505,555 | 3/1985 | Piller et al. | 359/389 |
| 4,815,835 | 3/1989 | Corona | 359/385 |
| 5,062,699 | 11/1991 | Hitchell | 359/801 |

Primary Examiner—James C. Housel
Assistant Examiner—Lien Tran
Attorney, Agent, or Firm—Nils H. Ljungman and Associates

[57] ABSTRACT

A portable diagnostic apparatus for the examination of biological material, in particular for the self-examination of a specimen containing substances which differ as a function of ovulation. The housing of the apparatus is designed such that the apparatus is of a size which allows the examining apparatus to be carried in the pockets of articles of clothing.

14 Claims, 2 Drawing Sheets

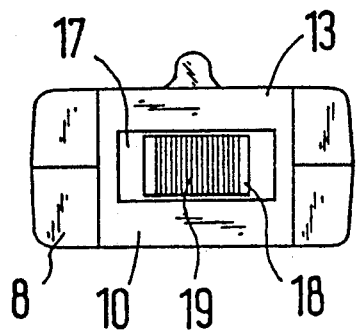
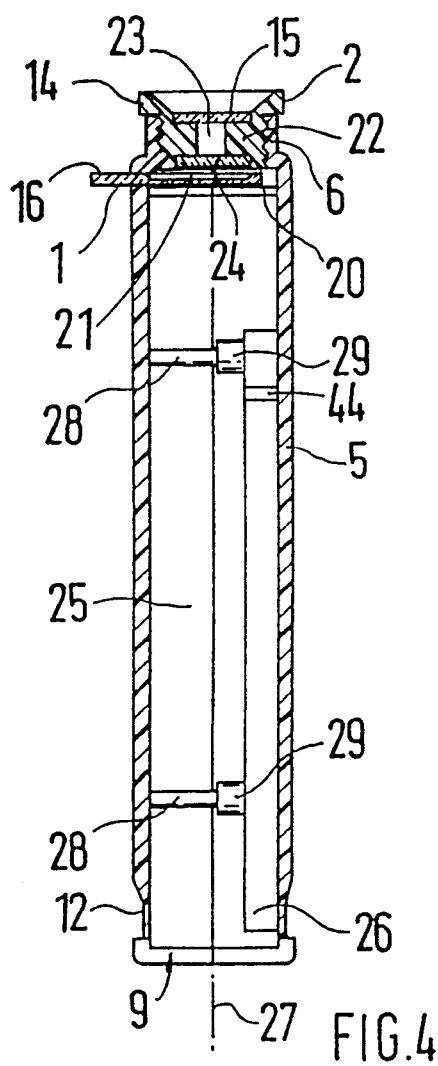
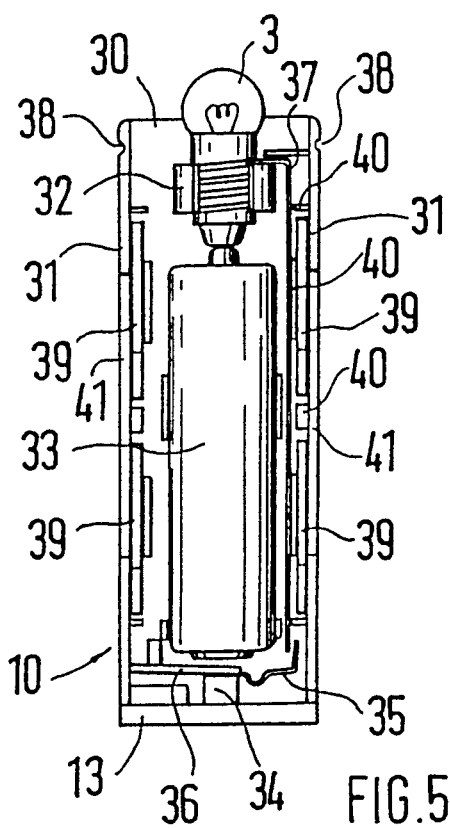

DIAGNOSTIC DEVICE FOR THE EXAMINATION OF BIOLOGICAL MATERIAL

BACKGROUND OF THE INVENTION

1. Field of the Invention

This invention relates to a portable diagnostic device for the examination of biological samples. In particular, one example of a use of such a portable examination device is for the examination of a biological specimen which contains substances related to ovulation. Because of the size and ease of operation of the device, the device is essentially suitable for use in self-administered examinations.

2. Background Information

One special application in which a portable and easy to use, self-examination device would generally be desirable is, for example, in the determination of a woman's fertile period. Such a determination could be very useful for any woman attempting to have a child, or more particularly, for instances in which a woman might be having difficulty in becoming pregnant. If a woman was more aware of when her fertile period was occurring, she would essentially know of the most appropriate time to attempt to become pregnant.

It is generally known that during a woman's fertile period, various additional bodily substances are formed which are not normally present in the body fluids, and it has been determined that some of these bodily substances can form special optical structures when dried. Thus, in order to help determine the ovulation period of women, it has been found that, if, during a woman's fertile period, a saliva sample is taken and dried, vein-like, or streaky structures are generally formed. During other periods, however, a dried saliva sample typically only shows a spotted, or dot-like pattern.

In general, these special optical structures can be seen upon magnification, so that upon visual examination, the presence or absence of these structures can essentially provide a "yes" or "no" answer regarding the occurrence of a woman's fertile period.

Examination devices which enables such bodily substances to be viewed, can be designed, for example, as microscopes or magnifying glasses, but on account of their design and construction, known devices are basically suitable, in particular, only for stationary operation. Typical known devices generally require special precautions against damage to guarantee correct long-term operation. In particular, the devices of the prior art are not suitable for use as portable devices for the performance of self-administered examinations.

OBJECT OF THE INVENTION

The object of the invention is therefore to improve a diagnostic device of the type described above, so that the device can be manufactured economically and so that the device can be used as a portable self-examination device.

SUMMARY OF THE INVENTION

This object is achieved by the present invention in that, the device of the present invention preferably provides, in a simple, hand-held device, a housing within which can be positioned an at least partly transparent slide, a radiant illumination device for illuminating the slide and positioned at some distance from the slide, and a lens system for optically magnifying the substances located on the slide. In particular, the housing of the device can be of a size which allows the device to be carried in the pockets of various articles of clothing, thereby allowing the device to be portable for use whenever use of the device is desired.

As a result of the configuration of the invention, it is possible to perform the test for determining a woman's fertile period at almost any desired place and time. In addition, on account of its compact design and construction, for example, the device can be carried in a pocket or in a handbag, and is essentially ready for use at any time. In one configuration of the invention, the saliva sample can be placed on the slide, and following a subsequent drying, it is possible, by means of the illumination apparatus, to generate the desired image brightness, and, by means of the lens system, to optically enlarge the specimen so that the specimen can be visually examined.

On account of the relatively simple structure and the relatively simple operation of the device according to the invention, the performance of the test for determining a woman's fertile period using the device of the present invention takes essentially very little time. In addition, in the event of an unclear test result, the test can be repeated as many times as desired within a relatively short period of time.

To make possible a simple mechanical arrangement and to guarantee sufficient ease of operation, the present invention proposes that the illumination apparatus be preferably located within the housing. This can essentially be done by preferably mounting the illumination device on a housing insert, which insert can easily be inserted into and removed from housing. In one particularly easy type of operation, the housing insert can preferably be inserted into the housing in the direction of the longitudinal axis of the housing.

To prevent an unintentional separation of the individual parts used, that is, the housing insert from the housing, the invention proposes that the housing insert preferably be provided with a catch for engaging an opposing member of the housing, thereby fixing the insert releasably in an inserted position within the housing.

Sufficient safety without the danger of interfering with the insertion process can be achieved if the catch preferably consists of at least one recess, which recess can be located in the vicinity of a side wall of the housing insert, and a corresponding latch or pin to engage the catch of the insert, which latch or pin can be located on an internal side wall of the housing.

To adjust the examination device to different optical conditions, and also to adjust the device to the different visual acuities of the users, the present invention proposes an embodiment in which the lens system is preferably equipped with at least one lens, and the lens is preferably movable towards and away from the slide to allow for adjustments in the visual clarity of the enlarged image of the sample.

A particularly simple optical adjustment can be achieved if the optics, which include at least one lens, are preferably arranged in or on a shaft equipped with an external thread, and this threaded shaft can be designed to preferably engage with an internal thread of a connecting piece of the housing. To alter the optical enlargement achievable by the lens system, without going exceedingly beyond the dimensions of the present invention, any feasible variety and combination of lenses can be used in the optical piece.

To make operation of the device according to the present invention as easy as possible, the present invention proposes an embodiment in which the slide can preferably be oriented so that it can be inserted laterally into the housing.

In addition, a defined positioning of the housing insert inside the housing can be possible because the housing preferably has guide elements extending in the direction of the longitudinal axis of the housing. These guide elements can essentially precisely guide the housing insert into the housing.

Another embodiment of the examination device makes it possible to grasp the housing with one hand while performing the operating procedures with the other hand. The present invention also proposes that, in the vicinity of a grip on the housing insert, there is preferably an actuator of a sliding switch for turning the illumination device on and off, which sliding switch, when the housing is held vertically with the lens arrangement on top, essentially is located on the bottom of the housing.

The housing insert can also provide storage space for storing additional slides. Thus, long-term usage of the magnification device can essentially be guaranteed because there can be a number of included replacement slides. In addition, because of the extra included slides, a few specimen samples could be prepared simultaneously to allow for quick cross-checking of the results of any one slide.

To provide an economical energy supply, the invention proposes that at least one battery preferably be located within the housing insert. This battery can essentially provide the power needed to light the illumination device, which illumination device can be a light bulb.

One aspect of the invention resides broadly in a portable diagnostic device for the examination of biological material, in particular for the examination of a specimen containing substances which are produced as a function of ovulation. The diagnostic device comprises: a housing having a first end and a second end with a longitudinal axis disposed along a length of the housing between the first end and the second end, and a transverse axis disposed along a width of the housing; a receptacle disposed within the housing for receipt of the biological material specimen, the receptacle being removable from the housing for placing the biological material specimen on the receptacle and removing the biological material specimen from the receptacle; a device for examining the biological material specimen, the device for examining the biological material specimen for being disposed at a first end of the housing; and an apparatus for enhancing examination of the biological material specimen.

Another aspect of the invention resides broadly in a portable diagnostic device for the examination of biological samples, the biological samples for being disposed on a receptacle, the diagnostic device comprising a housing, and the housing having a first end and a second end with a longitudinal axis disposed therebetween. The housing comprises: apparatus for holding the receptacle means within the housing; an apparatus for illuminating the samples on the receptacle; and a device for viewing the sample located on the receptacle means.

BRIEF DESCRIPTION OF THE DRAWINGS

Preferred embodiments of the invention are illustrated in the accompanying drawings, in which:

FIG. 3 is a view of the apparatus from below;

FIG. 4 is a cross section along Line IV—IV in FIG. 1; and

FIG. 5 is a view of the housing insert.

DESCRIPTION OF THE PREFERRED EMBODIMENTS

Figure 1:
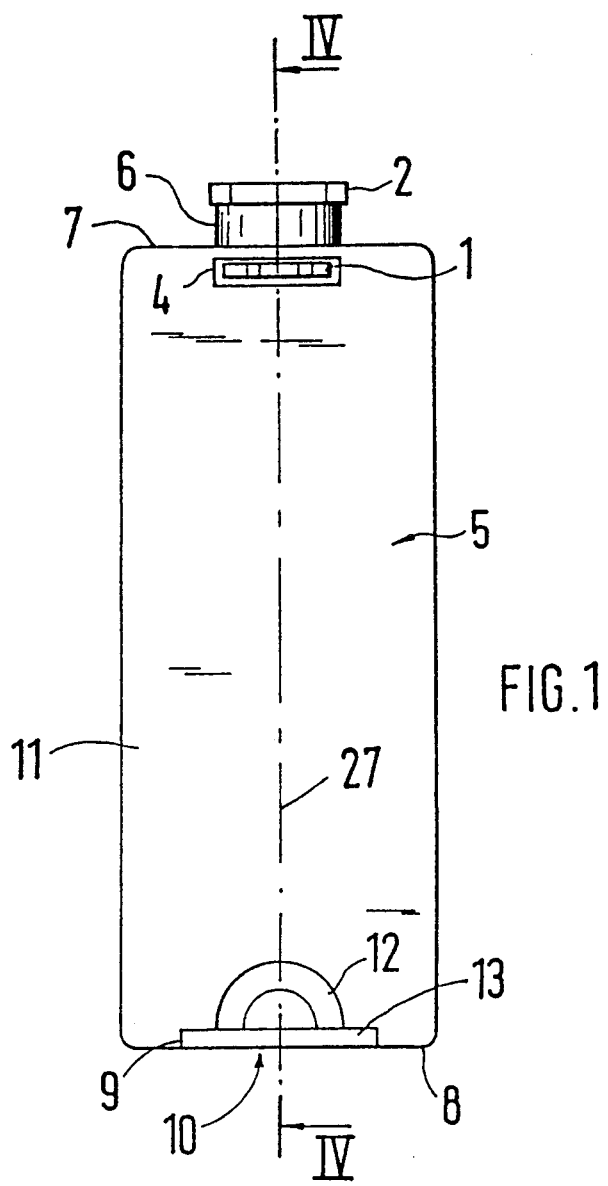
FIG. 1 is a side view of the magnification device.

The device for the examination of biological materials essentially has a slide 1, a lens system 2 and an illumination apparatus 3. In the embodiment illustrated in FIG. 1, the slide 1 can preferably be introduced into a shaft 4, which shaft 4 can be located in a front surface 11 of a housing 5. The lens system 2 can preferably be located in an upper region of the housing 5 when the housing 5 is arranged with its longitudinal axis 27 in the vertical direction. The lens system 2 can preferably be disposed on a connecting piece 6 which can rise above an upper edge 7 of the housing 5. In the vicinity of a lower edge 8 of the housing 5, with the housing arranged in the vertical direction as described above, there can preferably be a housing opening 9, into which a housing insert 10 can preferably be inserted. To facilitate the positioning of the housing insert 10 into the housing 5, there can be a recessed grip 12 located in a front surface 11 of the housing 5. The housing insert 10 can preferably be provided with a grip part 13 so that the grip part 13 projects beyond the recessed grip 12 to allow for easy manual grasping of the housing insert 10.

Figure 2:
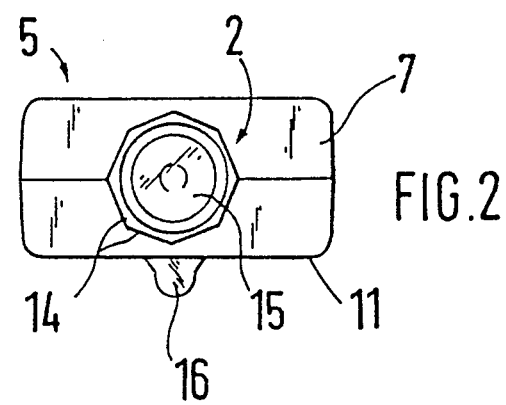
FIG. 2 is a top end view of the magnification device.

FIG. 2 shows that the lens system 2 can preferably be located on the top end 7 of the housing 5. This lens system 2 can preferably be provided with a canted edge 14 and at least an external lens 15. The edge 14, in the vicinity of its outer limit, can have a canted configuration to facilitate a manual turning of the lens system 2. The edge 14 can also be configured in other forms which prevent slipping of the users hand around the edge 14 when the lens system is being turned. Such an edge could therefore include a rubber coating or a single protruding flange. The slide 1 can preferably projects beyond the side wall 11 of the housing 5 by means of a positioning part 16. This positioning part 16 thus can facilitate placement, removal, and overall handling ability of the slide 1.

FIG. 3 shows that in the vicinity of the grip part 13 at end 8 of the housing, there can be a recess 17 in the housing insert. An actuator 18 of a sliding switch can preferably be movable guided in this recess 17. The actuator 18 can preferably be provided with a ribbing 19, or some other sort of friction enhancer, to increase user-friendliness and ease of operation by forming a substantially non-slip surface on the actuator.

FIG. 4 is a cross section which illustrates the internal structure of the housing 5. The slide 1 is shown preferably mounted and guided within the housing 5 by guide rails 20. In addition, the slide 1 can be provided with a recess 21 to hold the specimen. The connecting piece 6 is shown having an internal thread for engaging an external thread of a shaft piece 22. The lens system 2 can preferably be engaged with the shaft piece 22, so that the lens system can essentially be screwed into the connecting piece 6. Alternatively, the threaded portions could be reversed so that the lens system 2 could be screwed externally about the connecting piece 6.

The shaft 22 preferably has a hole 23 to optically connect the external lens 15 with an internal lens 24, if an internal lens is used. By turning the lens system 2 relative to the connecting piece 6, the distance between the slide 1 and the lens system 2 can be changed to thereby perform a focussing of the enlarged image of the specimen on the slide.

To guide the housing insert 10, as shown in detail in FIG. 5, into the housing 5, there are preferably guide elements 26 located within the housing inner chamber 25. These guide elements 26 preferably extend in the direction of a longitudinal axis 27 of the housing.

To simplify fabrication of the device, the housing 5 can be formed from two parts which are connected by means of transverse webs 28. These transverse webs 28 can be designed, for example, in the form of bolts, and the end of the webs 28 can be held by bushing-shaped counter elements 29, which elements 29 could be threaded for receipt of the bolts, whenever bolts are used.

FIG. 5 shows that the housing insert 10 preferably has a base plate 30 and side walls 31. These side walls 31 can each be connected to the grip part 13. The base plate 30 can be provided with a mounting 32 into which an illumination device 3 can be introduced and retained. The illumination device 3 can be a light bulb, for example. There can also be a battery 33 located within the insert 10 to supply power to the illumination device 3.

To make it possible to turn the illumination device 3 on and off, the actuator 18 of the sliding switch can be equipped with a cam 34. By means of the cam 34, a contact 35 can be displaced upon sliding of the actuator 18. The contact 35 can be electrically connected to one pole of the battery 33 by means of base contact 36 when the cam 34 is displaced by the actuator 18. When the cam 34 is moved, the contact 35 can be placed into contact with a connection contact 37, which connection contact 37 can be connected to a contact of the illumination device 3. The other contact of the illumination device 3 can be directly contacting the opposite pole of the battery 33.

To make possible a secure fastening of the housing insert 10 inside the housing 5, the housing insert preferably has recesses 38 located along the side walls 31. These recesses 38 preferably engage catches 44 after the housing insert 10 has been inserted a proper distance into the housing 5.

The housing insert 10 can also preferably have space for storing additional slides 39. These additional slides 39 can be oriented essentially parallel to the side walls 31, and can be protected from slipping by mounting elements 40. To facilitate the removal of the spare slides 39 from the insert 10, there can be tapers 41 located in the vicinity of the side walls 31.

One example of an examination procedure for examining saliva for substances characterizing ovulation phases can be performed in the following manner. First, a specimen of the saliva is placed into a recess 21 of a slide 1. The slide 1 can then be laterally inserted into the slot 4 of the housing 5, and the saliva can then be dried. Alternatively, the saliva could be dried before the slide is inserted into the housing. After the drying process has been completed, which drying process takes approximately three minutes, the lens system 2 can be turned relative to the connecting piece 6 to perform a focusing of the magnified image. The specimen can then be optically examined. To guarantee sufficient illumination of the specimen, the illumination apparatus 3 can be turned on by means of the actuator 18.

To evaluate the result of the examination, it is necessary to merely make a determination of whether there are crystalline structures in the vicinity of the dried saliva specimen. These crystalline structures would essentially appear as branched crystalline structures which resemble the patterns produced by frost on, for example, an automobile windshield. In the absence of the substances produced during a woman's fertile period, on the other hand, punctiform or spotty structures or soap-bubble-like structures would be formed.

To clean the slide 1 after the examination has been completed, the slide can be extracted laterally from the housing 5. If the slide 1 is worn or damaged, it can be replaced by one of the spare slides 39 stored within housing insert 10.

To make the device according to the present invention portable, so as to fit in the user's pockets, the overall dimensions of the device could be, for example, about 110 mm long, about 40 mm wide, and about 20 mm thick. This length of 110 mm can include the length of the lens system 2 which could be, for example about 8 mm. In addition, the diameter of the lens system 2 could be about 15 mm. The slot 4 into which the slide 1 is placed can be located about 2 mm below the upper edge 7 of the housing 5, and the slot 4 could have cross-sectional dimensions of about 3.5 mm in height, and about 16 mm in length. The dimensions of the housing insert 10 could be, for example, about 77 mm long, about 25 mm wide, and about 15 mm thick. Other dimensions, to accommodate various lens systems, illumination devices, battery sizes, etc., could also be possible as long as the overall size of the magnification device was not sufficiently increased so as to make the device too large to conceal or carry in a pocket.

In general, the device was essentially designed to fit conveniently into an average pocket, such as a shirt pocket or jacket pocket, or to fit conveniently into a hand of an average sized person, so as to make the device portable, unobtrusive, and essentially easy to use.

In summary, one feature of the invention resides broadly in an apparatus for the optical examination of biological material, in particular for the examination of a specimen containing substances which differ as a function of ovulation, characterized by the fact that in the vicinity of a housing 5 there is an at least partly transparent slide 1, an illumination apparatus 3 which can illuminate the slide in an internal housing chamber, and at some distance from a plane covered by the slide 1, a lens system 2 which optically magnifies the substances located on the slide 1, and by the fact that the housing 5 is of a size which allows it to be carried in the pockets of articles of clothing.

Another feature of the invention resides broadly in an apparatus characterized by the fact that the illumination apparatus 3 is located in the vicinity of a housing insert 10 which can be inserted into the housing.

Yet another feature of the invention resides broadly in an apparatus characterized by the fact that the housing insert 10 can be inserted into the housing 5 in the direction of a longitudinal axis 27 of the housing.

A further feature of the invention resides in an apparatus characterized by the fact that the housing insert 10 is equipped with a catch which releasably fixes it in an inserted position.

Another additional feature of the invention resides broadly in an apparatus characterized by the fact that the catch is formed by at least one recess 38, which is located in the vicinity of a side wall 31 of the housing insert 10.

Another additional feature of the invention resides broadly in an apparatus characterized by the fact that the lens system 2 is equipped with at least one lens which can be oriented at a variable distance relative to a plane covered by the slide 1.

Another additional feature of the invention resides broadly in an apparatus characterized by the fact that the lens system 2 has a shaft 22 provided with an external thread, which engages with an an internal thread of a connecting piece 6.

Another additional feature of the invention resides broadly in an apparatus characterized by the fact that the slide 1 is oriented so that it can be inserted laterally into the housing 5.

Another additional feature of the invention resides broadly in an apparatus characterized by the fact that to guide the housing insert 10 inside the housing 5, there are guide elements 26 extending in the direction of the longitudinal axis 27 of the housing.

Another additional feature of the invention resides broadly in an apparatus characterized by the fact that in the vicinity of a grip part 13 of the housing insert 10, there is an actuator 18, pointing downward in the perpendicular direction, as part of a sliding switch.

Another additional feature of the invention resides broadly in an apparatus characterized by the fact that in the vicinity of the housing insert 10 there is at least one spare slide 39.

Another additional feature of the invention resides broadly in an apparatus characterized by the fact that in the vicinity of the housing insert 10, there is at least one battery 33 to supply the illumination apparatus 3.

All, or substantially all, of the components and methods of the various embodiments may be used with at least one embodiment or all of the embodiments, if any, described herein.

All of the patents, patent applications and publications recited herein, if any, are hereby incorporated by reference as if set forth in their entirety herein.

The details in the patents, patent applications and publications may be considered to be incorporable, at applicant's option, into the claims during prosecution as further limitations in the claims to patentably distinguish any amended claims from any applied prior art.

The appended drawings, in their entirety, including all dimensions, proportions and/or shapes in at least one embodiment of the invention, are, if applicable, accurate and to scale and are hereby incorporated by reference into this specification.

The invention as described hereinabove in the context of the preferred embodiments is not to be taken as limited to all of the provided details thereof, since modifications and variations thereof may be made without departing from the spirit and scope of the invention.

What is claimed is:

1. A portable diagnostic device for examination of biological samples, the biological samples being disposed on receptacle means, said diagnostic device comprising:
   a housing having a first end and a second end with a longitudinal axis disposed therebetween, said housing comprising:
   means for holding said receptacle means within said housing; and
   means for viewing the sample located on the receptacle means; and
   a housing insert disposable within said housing, said housing insert being slidably removable from said housing;
   said housing comprising an opening for receipt of said housing insert;
   said housing insert comprising a support structure having mounted thereon;
   means for illuminating the sample on said receptacle means, said means for illuminating comprising a light source;
   a power supply for supplying power to said light source;
   circuit means for connecting said light source to said power supply;
   switch means for closing and opening said circuit means to switch said light source on and off; and
   means for holding and storing a plurality of said receptacle means.

2. The portable diagnostic device according to claim 1, wherein:
   said viewing means comprises at least one lens for producing a magnified image of the sample;
   said at least one lens being spaced a distance from said receptacle means; and
   said distance being adjustable for focusing the magnified image of the sample.

3. The portable diagnostic device according to claim 2, wherein said receptacle means comprises a slide having a contoured surface for receipt of the sample.

4. The portable diagnostic device according to claim 3, wherein said housing is of a size which allows the housing to fit in an average sized pocket.

5. The portable diagnostic device according to claim 4, wherein said housing has a length of about 110 mm, a width of about 40 mm, and a thickness of about 20 mm.

6. The portable diagnostic device according to claim 5, wherein:
   said at least one lens is disposed at said first end of said housing;
   said housing insert is disposable at said second end of said housing; and
   said slide is disposable within said housing between said at least one lens and said housing insert on said means for holding said receptacle means.

7. The portable diagnostic device according to claim 6, wherein:
   said opening for receipt of said housing insert is disposed in said second end of said housing;
   said housing insert is slidably insertable into said opening in said second end of said housing in a direction along the longitudinal axis of said housing;
   said housing comprises at least one guide for guiding said housing insert into said housing in the direction along the longitudinal axis of said housing; and
   said portable diagnostic device further comprises releasable locking means for retaining said housing insert in said housing.

8. The portable diagnostic device according to claim 7, wherein said releasable locking means comprises:
   at least one recess disposed on one of: said housing and said housing insert; and
   at least one projection disposed on the other of: said housing and said housing insert, said projection being disposable within said at least one recess for retaining said housing insert in said housing.

9. The portable diagnostic device according to claim 8, wherein:
said housing comprises a tubular projection disposed at said first end;
said lens system comprises a tubular element disposed at one of:
within said tubular projection of said housing; and
around said tubular projection of said housing.

10. The portable diagnostic device according to claim 9, wherein:
one of said tubular projection of said housing and said tubular element of said lens system comprises an external thread; and
the other of said tubular projection of said housing and said tubular element of said lens system comprises an internal thread threadable into said external thread to thereby movable adjust said distance between the slide and the lens system.

11. The portable diagnostic device according to claim 10, wherein said housing comprises at least a first wall portion parallel to the longitudinal axis of the housing, said first wall portion having an opening therein for receipt of said slide therein.

12. The portable diagnostic device according to claim 11, wherein:
said switch means is disposed at said second end of said housing when said housing insert is inserted into said housing; and
said power source comprises a battery.

13. A portable diagnostic device for examination of biological samples, the biological samples being disposed on a slide, said diagnostic device comprising:
a housing having a first end and a second end with a longitudinal axis disposed therebetween, said housing comprising:
means for holding said slide within said housing, said means for holding said slide being disposed between said first end and said second end of said housing, said slide being insertable into said housing on said means for holding said slide; and
a lens system for viewing the sample located on the slide, said lens system being disposable at said second end of said housing; and
a housing insert disposable within said housing, said housing insert being slidably removable from said housing;
said housing comprising an opening for receipt of said housing insert;
said housing insert being slidably insertable into said opening of said housing;
said housing insert comprising a support structure having mounted thereon;
means for illuminating the samples on said slide when said slide is inserted into said housing, said means for illuminating the samples being disposable at said first end of said housing, said means for illuminating comprising a light source;
a power supply for supplying power to said light source;
circuit means for connecting said light source to said power supply; and
switch means for closing and opening said circuit means to switch said light source on and off.

14. The portable diagnostic device according to claim 13, wherein:
said opening for receipt of said housing insert is disposed in said first end of said housing;
said housing insert is slidably insertable into said opening in said first end of said housing in the longitudinal direction of said housing;
said lens system is disposed a distance from said slide when said slide is inserted into said housing;
said distance between said slide and said lens system is adjustable for focusing the sample located on the slide; and
said housing insert further comprises means for holding and storing a plurality of said slides.

* * * * *

UNITED STATES PATENT AND TRADEMARK OFFICE
CERTIFICATE OF CORRECTION

PATENT NO. : 5,267,087
DATED : November 30, 1993
INVENTOR(S) : Peter WEIDEMANN

It is certified that error appears in the above-indentified patent and that said Letters Patent is hereby corrected as shown below:

In column 8, after line 9 and before line 10, Claim 1, insert the following paragraph:
        --said housing insert being slidably insertable into said opening of said housing;--.

In column 9, line 19, Claim 10, after 'thereby' delete "moveable" and insert --movably--.

Signed and Sealed this

Third Day of September, 1996

Attest:

BRUCE LEHMAN

Attesting Officer      Commissioner of Patents and Trademarks